(12) United States Patent
Winslow et al.

(10) Patent No.: US 7,622,439 B2
(45) Date of Patent: Nov. 24, 2009

(54) METHOD TO ENHANCE HEMODYNAMIC STABILITY USING OXYGEN CARRYING COMPOSITIONS

(75) Inventors: Robert M. Winslow, La Jolla, CA (US); Kim D. Vandegriff, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 0 days.

(21) Appl. No.: 12/260,945

(22) Filed: Oct. 29, 2008

(65) Prior Publication Data

US 2009/0075866 A1    Mar. 19, 2009

Related U.S. Application Data

(63) Continuation of application No. 11/218,006, filed on Aug. 31, 2005, now abandoned.

(60) Provisional application No. 60/605,816, filed on Aug. 31, 2004.

(51) Int. Cl.
*A61K 38/42* (2006.01)
*A61K 38/41* (2006.01)
*A61K 41/00* (2006.01)
*A01N 1/02* (2006.01)
*A61P 7/08* (2006.01)
*A61P 9/00* (2006.01)

(52) U.S. Cl. .................. 514/6; 514/8; 530/385
(58) Field of Classification Search .................. None
See application file for complete search history.

(56) References Cited

U.S. PATENT DOCUMENTS

| 6,432,918 | B1 * | 8/2002 | Winslow | 514/6 |
| 6,670,323 | B1 * | 12/2003 | Looker et al. | 514/6 |
| 7,101,846 | B2 * | 9/2006 | Winslow | 514/6 |
| 7,211,560 | B2 * | 5/2007 | Looker et al. | 514/6 |
| 2004/0072729 | A1 * | 4/2004 | Kwang et al. | 514/6 |

OTHER PUBLICATIONS

Cabrales et al., "Effects of Extreme Hemodilution with Hemoglobin-based $O_2$ Carriers on Microvascular Pressure," Am. J. Physiol. Heart Circ. Physiol., 2005, vol. 288: No. 5, pp. H2146-H2153.
Winslow et al., "Comparison of PEG-modified Albumin and Hemoglobin in Extreme Hemodilution in the Rat," J. Appl. Physiol., 2004, vol. 97, No. 4, pp. 1527-1534.

* cited by examiner

*Primary Examiner*—Lisa J Hobbs
(74) *Attorney, Agent, or Firm*—Laurie A. Axford; The Nath Law Group

(57) ABSTRACT

The present invention relates to methods for enhancing the hemodynamic stability of an individual undergoing surgery by administering a composition comprising a hemoglobin-based oxygen carrier. In one embodiment, the present invention relates to the use of polyalkylene oxide modified hemoglobins with reduced cooperativity and a high oxygen affinity to enhance oxygen offloading as a preventative measure to avoid hemodynamic stability-related complications during surgery.

9 Claims, 6 Drawing Sheets

METHOD TO ENHANCE HEMODYNAMIC STABILITY USING OXYGEN CARRYING COMPOSITIONS

CROSS REFERENCES TO RELATED APPLICATIONS

This application is a continuation application of U.S. Ser. No. 11/218,006, which was filed on Aug. 31, 2005 now abandoned, which claims the benefit of priority of U.S. provisional patent application Ser. No. 60/605,816 filed Aug. 31, 2004, each of which are incorporated herein by reference.

TECHNICAL FIELD

The present invention relates to methods for enhancing the hemodynamic stability of an individual undergoing surgery by administering a composition comprising a hemoglobin-based oxygen carrier. In one embodiment, the present invention relates to the use of polyalkylene oxide modified hemoglobins with reduced cooperativity and a high oxygen affinity to enhance oxygen offloading as a preventative measure to avoid hemodynamic stability-related complications during surgery.

BACKGROUND OF THE INVENTION

The blood is the means for delivering oxygen and nutrients and removing waste products from the tissues. The blood is composed of plasma in which red blood cells (RBCs or erythrocytes), white blood cells (WBCs), and platelets are suspended. Red blood cells comprise approximately 99% of the cells in blood, and their principal function is the transport of oxygen to the tissues and the removal of carbon dioxide therefrom.

The left ventricle of the heart pumps the blood through the arteries and the smaller arterioles of the circulatory system. The blood then enters the capillaries, where the majority of the delivery of oxygen, exchange of nutrients and extraction of cellular waste products occurs. (See, e.g., A. C. Guyton, "Human Physiology And Mechanisms Of Disease" (3rd. ed.; W. B. Saunders Co., Philadelphia. Pa.), pp. 228-229 (1982)). Thereafter, the blood travels through the venules and veins in its return to the right atrium of the heart. Though the blood that returns to the heart is oxygen-poor compared to that which is pumped from the heart, when at rest, the returning blood still contains about 75% of the original oxygen content.

The reversible oxygenation function (i.e., the delivery of oxygen) of RBCs is carried out by the protein hemoglobin. In mammals, hemoglobin has a molecular weight (MW) of approximately 64,000 Daltons and is composed of about 6% heme and 94% globin. In its native form, it contains two pairs of subunits (i.e., it is a tetramer), each containing a heme group and a globin polypeptide chain. In aqueous solution, hemoglobin is present in equilibrium between the tetrameric (MW 64,000 Daltons) and dimeric (MW 32,000 Daltons) forms. Outside of the RBC, the dimers are prematurely excreted by the kidney (plasma half-life of approximately 2-4 hours). Along with hemoglobin, RBCs contain stroma (the RBC membrane), which comprises proteins, cholesterol, and phospholipids.

Due to the demand for blood products in hospitals and other settings, extensive research has been directed at the development of blood substitutes. A "blood substitute" is a blood product that is capable of carrying and supplying oxygen to the tissues. Hemoglobin-based oxygen carriers (HBOCs) are blood substitutes containing hemoglobins. HBOCs have a number of uses, including replacing blood lost during surgical procedures and following acute hemorrhage, and for resuscitation procedures following traumatic injury. Essentially, HBOCs can be used for any purpose in which banked blood is currently administered to patients. (See, e.g., U.S. Pat. Nos. 4,001,401 to Bonson et al., and 4,061,736 to Morris et al.)

The development of HBOCs is especially important, given the fact that the current human blood supply is limited. For this reason, human blood is normally only used in circumstances when it is medically necessary. This usually means that human blood is not appropriate for prophylactic use, such as "blood doping" (i.e. administering whole blood for the purpose of enhancing performance by increasing the oxygen carrying capacity of the blood). Accordingly, neither the use of whole blood nor HBOCs for prophylactic indications are widespread, and in most cases are considered to be a somewhat questionable practice.

The administration of HBOCs to patients prior to surgery has been previously suggested in combination with the removal of autologous blood from the patients (i.e. acute normovolemic hemodilution or "ANH") which could be returned later in the procedure, if needed, or after surgery. See, for example, PCT WO 98/37909. Such patients are considered herein not to be "normovolemic" at the time of surgery. However, this procedure does not address the need for prophylactic measures to avoid the detrimental primary effects of surgical procedures such as hemodynamic stability, and only addresses the secondary effects of blood loss associated with surgery.

Enhancing hemodynamic stability during surgery requiring general anesthesia is important for two fundamental reasons. First, hemodynamic instability caused by blood loss or other factors can lead to tissue damage and even death. For example, hemorrhagic hypotension and anaphylactic shock are conditions which result from significant blood loss leading to reduced tissue oxygenation. For patients with such medical conditions, it is desirable and often critical for their survival to stabilize their blood pressure and to increase the amount of oxygen provided to body tissues by their circulatory systems.

Second and most importantly, hemodynamic instability, even minor and transient, may affect a patient's post-surgical recovery. This instability may occur anywhere throughout the body, and is often manifested as a "hypotensive event," which is usually recorded as a decrease in blood pressure. Such events can occur as a result of fluctuations of localized hemodynamic properties during general anesthesia, even when there is no loss of blood. These events can cause cognitive damage and other complications that exacerbate recovery following surgery. For example, elderly patients undergoing invasive surgical procedures such as hip replacements would benefit from any prophylactic treatment that would enhance their hemodynamic stability during surgery. In addition, such patients are often not suitable candidates for ANH, and enhancing their hemodynamic stability would be expected to lessen their need for transfusions using donor blood.

The use of plasma expanders and volume replacements to maintain hemodynamic stability is widespread. However, these non-oxygen carrying solutions only dilute the oxygen capacity of the blood, even without concomitant ANH, and may actually cause hemodynamic instability in some instances. In addition to plasma expanders and volume replacements, crystalloid solutions have also been suggested for use in maintaining hemodynamic stability. However, the administration of these solutions may result in excessive water retention and edema, which can also cause fluctuations in hemodynamic properties.

Accordingly, there is a need for methods to enhance hemodynamic stability which may result in transient hypotensive events that do not diminish the blood's inherent oxygen carrying capacity. In accordance with this goal, the present invention relates to a method of enhancing hemodynamic stability by administering compositions comprising hemoglobin-based oxygen carriers such as specially formulated polyalkylene oxide modified hemoglobins.

SUMMARY OF THE INVENTION

The present invention relates to the use of a composition in the treatment of a normovolemic subject undergoing surgery to enhance hemodynamic stability. In one embodiment, the invention relates to a method for enhancing hemodynamic stability of a normovolemic subject undergoing surgery comprising: a) administering a composition containing a hemoglobin-based oxygen carrier (HBOC) with an oxygen affinity higher than whole blood to the subject in connection with the surgery; and b) monitoring the hemodynamic stability of the patient. Such administration may occur prior to, during or after surgery, or any combination thereof. In addition, the hemodynamic stability may be measured before, during or after surgery, or any combination thereof. In addition, monitoring the hemodynamic stability of the patient may take many forms, such as monitoring the blood pressure of a patient in one embodiment, hemodynamic stability is characterized by systolic pressure remaining above 90 mm Hg.

The HBOC of the present invention may take many forms, such as polyalkylene oxide modified hemoglobin, which may be obtained from natural or synthetic sources, including recombinant sources. In addition the source of hemoglobin may be from humans or other non-human animals.

In another embodiment of the present invention, the HBOC has an oxygen affinity greater than twice that of whole blood, which may include HBOCs with P50s between 4 to 15.

Other aspects of the invention are described throughout the specification.

DETAILED DESCRIPTION OF THE INVENTION

Figure 1:
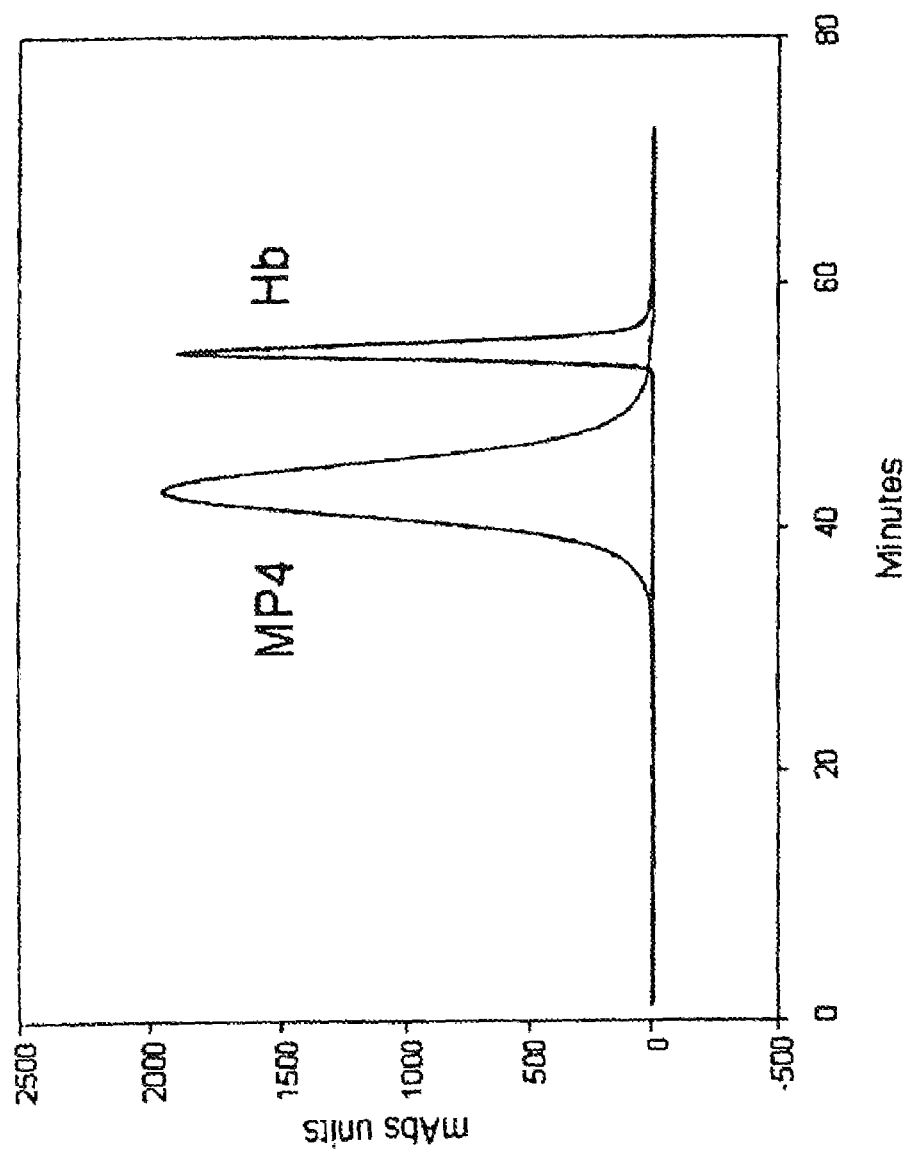
FIG. 1 depicts the FPLC chromatogram of MalPEG-Hb and stroma free hemoglobin (SFH).

The present invention relates to methods for enhancing the hemodynamic stability of an individual undergoing surgery by administering a composition comprising a hemoglobin-based oxygen carrier. In one embodiment, the present invention relates to the use of polyalkylene oxide modified hemoglobins with reduced cooperativity and a high oxygen affinity to enhance oxygen offloading as a preventative measure to avoid hemodynamic stability-related complications during surgery.

To facilitate understanding of the invention set forth in the disclosure that follows, a number of terms are defined below.

DEFINITIONS

The term "hemoglobin" refers generally to the protein contained within red blood cells that transports oxygen. Each molecule of hemoglobin has 4 subunits, 2 α chains and 2 β chains, which are arranged in a tetrameric structure. Each subunit also contains one heme group, which is the iron-containing center that binds oxygen. Thus, each hemoglobin molecule can bind 4 oxygen molecules.

The term "modified hemoglobin" includes, but is not limited to, hemoglobin altered by a chemical reaction such as intra- and inter-molecular cross-linking, genetic manipulation, polymerization, and/or conjugation to other chemical groups (e.g., polyalkylene oxides, for example polyethylene glycol, or other adducts such as proteins, peptides, carbohydrates, synthetic polymers and the like). In essence, hemoglobin is "modified" if any of its structural or functional properties have been altered from its native state. As used herein, the term "hemoglobin" by itself refers both to native, unmodified, hemoglobin, as well as modified hemoglobin.

The term "surface-modified hemoglobin" is used to refer to hemoglobin described above to which chemical groups such as dextran or polyalkylene oxide have been attached, most usually covalently. The term "surface modified oxygenated hemoglobin" refers to hemoglobin that is in the "R" state when it is surface modified.

The term "stroma-free hemoglobin" refers to hemoglobin from which all red blood cell membranes have been removed.

The term "methemoglobin" refers to an oxidized form of hemoglobin that contains iron in the ferric state and cannot function as an oxygen carrier.

The term "MalPEG-Hb" refers to hemoglobin to which malemidyl-activated PEG has been conjugated. Such MalPEG may be further referred to by the following formula:

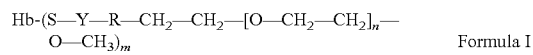

$$\text{Hb-(S—Y—R—CH}_2\text{—CH}_2\text{—[O—CH}_2\text{—CH}_2]_n\text{—O—CH}_3)_m \qquad \text{Formula I}$$

where Hb refers to tetrameric hemoglobin, S is a surface thiol group, Y is the succinimido covalent link between Hb and Mal-PEG, R is absent or is an alkyl, amide, carbamate or phenyl group (depending on the source of raw material and the method of chemical synthesis), [O—CH$_2$—CH$_2$]$_n$ are the oxyethylene units making up the backbone of the PEG polymer, where n defines the length of the polymer (e.g., MW= 5000), and O—CH$_3$ is the terminal methoxy group.

The term "plasma expander" refers to any solution that may be given to a subject to increase plasma volume.

The term "oxygen carrying capacity," or simply "oxygen capacity," of a blood substitute refers to its capacity to carry oxygen, but does not necessarily correlate with the efficiency in which it delivers oxygen. Oxygen carrying capacity of a hemoglobin-containing blood substitute is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl. Hemoglobin concentration can be measured by any known method, such as by using the β-Hemoglobin Photometer (HemoCue, Inc., Angelholm, Sweden.) Similarly, oxygen capacity can be measured by the amount of oxygen released from a sample of hemoglobin or blood by using, for example, a fuel cell instrument (e.g., Lex-$O_2$-Con, Lexington Instruments, Waltham, Mass.)

The term "oxygen affinity" refers to the avidity with which an oxygen carrier such as hemoglobin binds molecular oxygen. This characteristic is defined by the oxygen equilibrium curve which relates the degree of saturation of hemoglobin molecules with oxygen (Y axis) with the partial pressure of oxygen (X axis). The position of this curve is denoted by the value, P50, the partial pressure of oxygen at which the oxygen carrier is half-saturated with oxygen, and is inversely related to oxygen affinity. Hence the lower the P50, the higher the oxygen affinity. The oxygen affinity of whole blood (and components of whole blood such as red blood cells and hemoglobin), as well as any oxygen carrier, can be measured by a variety of methods known in the art. (See, e.g., Winston et at, *J. Biol. Chem.* 252(7):2331-37 (1977)). Oxygen affinity may also be determined using a commercially available HEM OX™ Analyzer (TCS Scientific Corporation, New Hope, Pa.). (See, e.g., Vandegriff and Shrager in "Methods in Enzymology" (Everse et al., Eds.) 232:460 (1994)).

The term "oxygen-carrying component" refers broadly to a substance capable of carrying oxygen in the body's circulatory system and delivering at least a portion of that oxygen to the tissues. In preferred embodiments, the oxygen-carrying component is native or modified hemoglobin, and is also referred to herein as a "hemoglobin-based oxygen carrier," or "HBOC."

The term "hemodynamic parameters" refers broadly to measurements indicative of blood pressure, flow and volume status, including direct measurements such as blood pressure, cardiac output, right atrial pressure, left ventricular end diastolic pressure, as well as indirect measurements of tachycardia, ischemia, bradycardia, conduction problems, fluid balance, weight, ICU time and kidney function.

The term "crystalloid" refers to small molecules (usually less than 10 Å) such as salts, sugars, and buffers. Unlike colloids, crystalloids do not contain any oncotically active components and equilibrate in between the circulation and interstitial spaces very quickly.

The term "colloid" (in contrast to "crystalloid") refers to larger molecules (usually greater than 10 Å) that equilibrate across biological membranes depending on their size and charge and includes proteins such as albumin and gelatin, as well as starches such as pentastarch and hetastarch.

The term "colloid osmotic pressure" refers to the pressure exerted by a colloid to equilibrate fluid balance across a membrane.

The term "stable to autooxidation" refers to the ability of a HBOC to maintain a low rate of autoxidation. A HBOC is considered stable at 24° C. if the methemoglobin/total hemoglobin ratio does not increase more than 2% after 10 hours at room temperature (approximately 24° C.) For example, if the rate of autoxidation is 0.2 $hr^{-1}$, then if the initial percentage of methemoglobin is 5%, and the HBOC would be considered stable at room temperature for 10 hours if this percentage did not increase above 7%.

The term "methemoglobin/total hemoglobin ratio" refers to the ratio of oxidized hemoglobin to total hemoglobin.

The term "mixture" refers to a mingling together of two or more substances without the occurrence of a reaction by which they would lose their individual properties; the term "solution" refers to a liquid mixture; the term "aqueous solution" refers to a solution that contains some water and may also contain one or more other liquid substances with water to form a multi-component solution; the term "approximately" refers to the actual value being within a range, e.g. 10%, of the indicated value.

The term "polyethylene glycol" or "PEG" refers to liquid or solid polymers of the general chemical formula $H(OCH_2CH_2)_nOH$, where n is greater than or equal to 4, and variants thereof, such as PEG that is activated, substituted and/or unsubstituted.

The term "perfusion" refers to the flow of fluid to tissues and organs through arteries and capillaries.

The term "hemodynamic stability" refers to stable functioning in the mechanics of circulation, i.e. the stability over a given period of time of any hemodynamic parameter.

The term "hypotensive events" is characterized by or due to localized or generalized hypotension, i.e. a lowering of blood pressure, which can further be defined quantitatively as a systolic pressure less than 90 mmHg or a reduction of blood pressure below 75% of the baseline value.

The meaning of other terminology used herein should be easily understood by someone of reasonable skill in the art.

The Nature of Oxygen Delivery and Consumption

Although the successful use of the compositions and methods of the present invention do not require comprehension of the underlying mechanisms of oxygen delivery and consumption, basic knowledge regarding some of these putative mechanisms may assist in understanding the discussion that follows. It has generally been assumed that the capillaries are the primary conveyors of oxygen to the tissue. However, regarding tissue at rest, current findings indicate that there is approximately an equipartition between arteriolar and capillary oxygen release. That is, hemoglobin in the arterial system is believed to deliver approximately one third of its oxygen content in the arteriolar network and one-third in the capillaries, while the remainder exits the microcirculation via the venous system.

The arteries and arterioles themselves are sites of oxygen utilization. For example, the artery wail requires energy to effect regulation of blood flow through contraction against vascular resistance. Thus, the arterial wall is normally a significant site for the diffusion of oxygen out of the blood. However, current oxygen-delivering compositions (e.g., HBOCs) may release too much of their oxygen content in the arterial system, and thereby induce an autoregulatory reduction in capillary perfusion. Accordingly, the efficiency of oxygen delivery of a blood substitute may actually be hampered by having too much oxygen or too low an oxygen affinity.

The rate of oxygen consumption by the vascular wall, i.e., the combination of oxygen required for mechanical work and oxygen required for biochemical synthesis, can be determined by measuring the gradient at the vessel wall. See, e.g., Winslow, et al., in "Advances in Blood Substitutes" (1997), Birkhauser, Ed., Boston, Mass., pages 167-188. Present technology allows accurate oxygen partial pressure measurements in a variety of vessels. The measured gradient is directly proportional to the rate of oxygen utilization by the tissue in the region of the measurement. Such measurements show that the vessel wall has a baseline oxygen utilization which increases with increases in inflammation and constriction, and is lowered by relaxation.

The vessel wall gradient is inversely proportional to tissue oxygenation. Vasoconstriction increases the oxygen gradient (tissue metabolism), while vasodilation lowers the gradient. Higher gradients are indicative of the fact that more oxygen is used by the vessel wall, while less oxygen is available for the tissue. The same phenomenon is believed to be present throughout the microcirculation.

The Relationship Between Vasoconstriction and Oxygen Affinity

The rationale for developing an HBOC with high oxygen affinity is based, in part, on past studies using cell-free hemoglobins as alternatives to red blood cell transfusions. Some of the physiological effects of these solutions remain incompletely understood. Of these, perhaps the most controversial is the propensity to cause vasoconstriction, which may be manifest as hypertension in animals and man (Amberson, W., "Clinical experience with hemoglobin-saline solutions,". *Science* 106: 117-117 (1947)) (Keipert, P., A. Gonzales, C. Gomez, V. Macdonald, J. Hess, and R. Winslow, "Acute changes in systemic blood pressure and urine output of conscious rats following exchange transfusion with diaspirin-crosslinked hemoglobin solution,"*Transfusion* 33:701-708, (1993)). Human hemoglobin crosslinked between α chains with bis-dibromosalicyl-fumarate (ααHb) was developed by the U.S. Army as a model red cell substitute, but was abandoned by the Army after demonstration of severe increases in pulmonary and systemic vascular resistance (Hess, J., V. Macdonald, A. Murray, V. Coppes, and C. Gomez, "Pulmonary and systemic hypertension after hemoglobin administration" *Blood* 78: 356A (1991)). A commercial version of this product was also abandoned after a disappointing Phase III clinical trial (Winslow, R. M. "αα-Crosslinked hemoglobin: Was failure predicted by preclinical testing?" *Vox sang* 79: 1-20 (2000).

The most commonly advanced explanation for the vasoconstriction produced by cell-free hemoglobin is that it readily binds the endothelium-derived relaxing factor, nitric oxide (NO). In fact, recombinant hemoglobins with reduced affinity for NO have been produced which appear to be less hypertensive in top-load rat experiments (Doherty, D. H., M, P. Doyle, S. R. Curry, R. J. Vali, T. J. Fattor, J. S. Olson, and D. D. Lemon, "Rate of reaction with nitric oxide determines the hypertensive effect of cell-free hemoglobin," *Nature Biotechnology* 16: 672-676 (1998)) (Lemon, D. D., D. H. Doherty, S. R. Curry, A. J. Mathews, M. P. Doyle, T. J. Fattor, and J. S. Olson, "Control of the nitric oxide-scavenging activity of hemoglobin," *Art Cells, Blood Subs., and Immob. Biotech* 24:378 (1996)).

However, studies suggest that NO binding may not be the only explanation for the vasoactivity of hemoglobin. It has been found that certain large hemoglobin molecules, such as those modified with polyethylene glycol (PEG), were virtually free of the hypertensive effect, even though their NO binding rates were identical to those of the severely hypertensive ααHb (Rohlfs, R, J., E. Bruner, A. Chiu, A. Gonzales, M. L. Gonzales, D. Magde, M. D. Magde, K. D. Vandegriff, and R. M. Winslow, "Arterial blood pressure responses to cell-free hemoglobin solutions and the reaction with nitric oxide," *J Biol Chem* 273: 12128-12134 (1998)). Furthermore, it was found that PEG-hemoglobin was extraordinarily effective in preventing the consequences of hemorrhage when given as an exchange transfusion prior to hemorrhage (Winslow, R. M., A. Gonzales, M. Gonzales, M. Magde, M. McCarthy, R. J. Rohlfs, and K. D. Vandegriff "Vascular resistance and the efficacy of red cell substitutes," *J Appl Physiol* 85: 993-1003 (1998)).

This protective effect correlated with the lack of hypertension, suggesting that vasoconstriction is responsible for the disappointing performance of many of the hemoglobin-based products studied to date. Based on these observations, a hypothesis was developed to explain vasoconstriction, as an alternative, or possibly in addition to, the effect of NO binding. Although not wishing to be bound by any particular theory, it is believed that a substantial component of hemoglobin's vasoactive effect is a reflexive response to the diffusion of hemoglobin in the cell-free space. This hypothesis was tested in an in vitro capillary system, and it was demonstrated that PEG-hemoglobin, which has a reduced diffusion constant, transferred $O_2$ in a manner very similar to that of native red blood cells (McCarthy, M. R., K. D. Vandegriff, and R. M. Winslow, "The role of facilitated diffusion in oxygen transport by cell-free hemoglobin: Implications for the design of hemoglobin-based oxygen carriers," *Biophysical Chemistry* 92: 103-117 (2001)). Oxygen affinity would be expected to play a role in its facilitated diffusion by hemoglobin in the plasma space, since the change in saturation from the hemoglobin to the vessel wall is a determinant of the diffusion gradient of the hemoglobin itself.

Oxygen affinity of cell-free hemoglobin may play an additional role in the regulation of vascular tone, since the release of $O_2$ to vessel walls in the arterioles will trigger vasoconstriction (Lindbom, L., R. Turna, and K. Arfors, "Influence of oxygen on perfusion capillary density and capillary red cell velocity in rabbit skeletal muscle," *Microvasc Res* 19:197-208 (1980)). In the hamster skinfold, the $PO_2$ in such vessels is in the range of 20-40 Torr, where the normal red cell oxygen equilibrium curve is steepest (Intaglietta, M., P. Johnson, and R. Winslow, "Microvascular and tissue oxygen distribution," *Cardiovasc Res* 32: 632-643 (1996)). Thus from a theoretical point of view, it may be important for the P50 of cell-free hemoglobin to be lower than that of red cells (i.e., higher $O_2$ affinity), in order to prevent release of $O_2$ in arteriolar regulatory vessels.

Oxygen Offloading

In addition to oxygen affinity, the oxygen binding properties themselves, i.e. the cooperativity and allosteric effects, may play a crucial role in the oxygen offloading capabilities of HBOCs. It has been observed that polyalkylene binding to hemoglobin results in a general "tightening" of the globin structure. This is attributed, to the osmotic effects of having a hydrophilic shell surrounding the hemoglobin, and may also depend on the nature and location of the linking groups used to attach the polyalkylene oxide. Most conventional wisdom is that the design of HBOCs should mimic the characteristics of native hemoglobin. However, it has unexpectedly been found that perturbation of the quaternary conformation of the hemoglobin can have advantages, particularly in the context of oxygen offloading.

A protein is considered to be "allosteric" if its characteristics change as a result of binding to an effector molecule, i.e. a ligand, at its allosteric site. In the case of hemoglobin, the ligand is oxygen. Each subunit of the hemoglobin tetramer is capable of binding one oxygen molecule. Each subunit also exists in one of two conformations—tensed (T) or relaxed (R). In the R state, it can bind oxygen more readily than in the T state.

Hemoglobin exhibits a concerted effect, or cooperativity, among individual submits binding oxygen. The binding of oxygen to one subunit induces a conformational change in that subunit that causes the remaining active sites to exhibit an enhanced oxygen affinity. Accordingly, each sequential oxygen molecule that binds to the hemoglobin molecule attaches more readily than the one before, until the hemoglobin molecule has achieved the R, or "liganded" state, with four attached oxygen molecules.

In the reverse, native hemoglobin exhibits a concerted effect in terms of its efficiency to release oxygen. The first molecule is more tightly attached and takes more energy to be "offloaded" then the next one, and so on. Accordingly, the conventional teachings towards the design of blood substitutes that mimic the cooperativity of native hemoglobin may adversely affect its ability to release oxygen once bound.

The present invention relates to the finding that HBOCs with less, not more, cooperativity than native hemoglobin are unexpectedly more useful in applications involving oxygen offloading. Accordingly, a composition for use in enhancing hemodynamic stability must be able to readily release its oxygen once it arrives at its target location, but must not contain too much oxygen releasing capacity to avoid vasoconstrictive effects. In summary, the ideal composition for prophylactic treatment in connection with a surgical procedure to enhance hemodynamic stability necessarily contains a modified hemoglobin with less cooperativity than native hemoglobin, but which is formulated in a composition with a much higher oxygen affinity (e.g. less man half the P50) when compared to whole blood.

Oxygen-Carrying Component

In preferred embodiments, the oxygen carrier (i.e., the oxygen-carrying component) is a hemoglobin-based oxygen carrier, or HBOC. The hemoglobin may be either native (unmodified); subsequently modified by a chemical reaction such as intra- or inter-molecular cross-linking, polymerization, or the addition of chemical groups (e.g., polyalkylene oxides, or other adducts); or it may be recombinantly engineered. Human alpha- and beta-globin genes have both been cloned and sequenced. Liebhaber, et al, P.N.A.S. 77: 7054-7058 (1980); Marotta, et al, J. Biol. Chem. 353: 5040-5053 (1977) (beta-globin cDNA). In addition, many recombinantly produced modified hemoglobins have now been produced using site-directed mutagenesis, although these "mutant" hemoglobin varieties were reported with high oxygen affinities. See, e.g., Nagai, et al., P.N.A.S., 82:7252-7255 (1985).

The HBOCs that are used in the practice of the present invention have oxygen affinities higher than normal whole blood (from the same animal source as the subject, which may not necessarily be a human), which is also expressed as a P50 lower than that of whole blood. Whole blood is generally considered to have a P50 approximating 28 torr. In one embodiment, the HBOCs of the present invention have a P50 less than half that of whole blood, which is considered to be a "high oxygen affinity." Such high oxygen affinity HBOCs may have a P50 of 4-15, such as 10, 7, etc.

The present invention is not limited by the source of the hemoglobin. For example, the hemoglobin may be derived from animals and humans. Preferred sources of hemoglobin for certain applications are humans, cows and pigs, as well as non-mammalian sources, such as annelids, reptiles, etc. In addition, hemoglobin may be produced by other methods, including chemical synthesis and recombinant techniques. The hemoglobin can be added to the blood product composition in free form, or it may be encapsulated in a vesicle, such as a synthetic particle, microballoon or liposome. The preferred oxygen-carrying components of the present invention should be stroma free and endotoxin free. Representative examples of oxygen-carrying components are disclosed in a number of issued U.S. patents, including U.S. Pat. No. 4,857,636 to Hsia; U.S. Pat. No. 4,600,531 to Walder, U.S. Pat. No. 4,061,736 to Morris et al.; U.S. Pat. No. 3,925,344 to Mazur; U.S. Pat. No. 4,529,719 to Tye; U.S. Pat. No. 4,473,496 to Scannon; 4,584,130 to Bocci et al; U.S. Pat. No. 5,250,665 to Kluger, et al.; U.S. Pat. No. 5,028,588 to Hoffman et al and U.S. Pat. No. 4,826,811 and U.S. Pat. No. 5,194,590 to Sehgal et al.

In addition to the aforementioned sources of hemoglobin, it has recently been found that horse hemoglobin may have certain advantages as the oxygen carrying component in the compositions of the present invention. One advantage is that commercial quantities of horse blood are readily available from which horse hemoglobin can be purified. Another unexpected advantage is that horse hemoglobin exhibits chemical properties that may enhance its usefulness in the blood substitutes of the present invention.

Previous reports have indicated that horse hemoglobin auto-oxidizes to methemoglobin faster than human hemoglobin, which would make it less desirable as a blood substitute component. See, e.g., J. G. McLean and I. M. Lewis, Research in Vet Sci., J9:259-262 (1975). In order to minimize auto-oxidation, McLean and Lewis used a reducing agent, glutathione, after red blood cell lysis. However, the hemoglobin that is used to prepare the compositions of the present invention, regardless of whether the source of hemoglobin is human or horse, do not require the use of reducing agents to prevent auto-oxidation after red blood cell lysis.

More recently, it has been reported that horse hemoglobin has an oxygen affinity that is different from that of human hemoglobin. See, e.g., M. Mellegrini, et al. Eur. J. Biochem., 268: 3313-3320 (2001). Such a difference would discourage the selection of horse hemoglobin to prepare blood substitutes that mimic human hemoglobin. However, when incorporated into the compositions of the present invention, no significant difference (less than 10%) in oxygen affinity between human and horse hemoglobin-containing conjugates is observed. Accordingly, contrary to these seemingly undesirable properties, in the compositions of the present invention, horse hemoglobin may be equivalent to human hemoglobin.

For use in the present invention, the HBOC has an oxygen affinity that is greater than whole blood, and preferably twice that of whole blood, or alternatively, greater than that of stroma-free hemoglobin (SFH), when measured under the same conditions. In most instances, this means that the HBOC in the blood substitute will have a P50 less than 10, and more preferably less than 7. In the free state, SFH has a P50 of approximately 15 torr, whereas the P50 for whole blood is approximately 28 torr. It has previously been suggested that increasing oxygen affinity, and thereby lowering the P50, may enhance delivery of oxygen to tissues, although it was implied that a P50 lower than that of SFH would not be acceptable. See Winslow, et al., in "Advances in Blood Substitutes" (1997), Birkhauser, ed., Boston, Mass., at page 167, and U.S. Pat. No. 6,054,427. This suggestion contradicts the widely held belief that modified hemoglobins for use as blood substitutes should have lower oxygen affinities, and should have P50s that approximate that of whole blood. Hence, many researchers have used pyridoxyl phosphate to raise the P50 of SFH from 10 to approximately 20-22, since pyridoxylated hemoglobin more readily releases oxygen when compared to SFH.

There are many different scientific approaches to manufacturing HBOCs with high oxygen affinity (i.e. those with P50s less than SFH). For example, studies have identified the amino acid residues that play a role in oxygen affinity, such as 0-93 cysteine, and thus site-directed mutagenesis can now be easily carried out to manipulate oxygen affinity to the desired level. See, e.g., U.S. Pat. No. 5,661,124. Many other approaches are discussed in U.S. Pat. No. 6,054,427.

Hemoglobin-Associated Toxicity

Hemoglobin is known to exhibit autooxidation when it reversibly changes from the ferrous ($Fe^{2+}$) to the ferric ($Fe^{3+}$) or methemoglobinform. When this happens, molecular oxygen dissociates from the oxyhemoglobin in the form a superoxide anion ($O_2^-$). This also results in destabilization of the heme-globin complex and eventual denaturation of the globin chains. Both oxygen radical formation and protein denaturation are believed to play a role in in vivo toxicity of HBOCs (Vandegriff, K. D, Blood Substitutes, Physiological Basis of Efficacy, pages 105-130, Winslow et al., ed., Birkhauser, Boston, Mass. (1995).)

With most HBOCs, there is a negative correlation between oxygen affinity and hemoglobin oxidation, i.e., the higher the oxygen affinity, the lower the rate of autooxidation. However, the effects of different hemoglobin modifications on oxygen affinity and the rate of autooxidation are not always predictable. In addition, the optimal balance between oxygen affinity and autooxidation rate is not well understood.

In one embodiment, the compositions of the present invention contain polyalkylene oxide-Hb conjugates, such as polyethylene glycol-Hb conjugates that exhibit very low rates of autooxidation at room temperature. When measured as a rate of oxidation, this value should be as low as possible (i.e., 0.2% per hour of total hemoglobin, more preferably 0.1% per hour of total hemoglobin, at room temperature for at least 3 hours, and more preferably at least 10 hours.) Thus, exemplary HBOCs of the present invention remain stable during administration and/or storage at room temperature.

Modifications of the Oxygen-Carrying Component

In an exemplary embodiment, the oxygen-carrying component is polyalkylene oxide (PAO) modified hemoglobin. Suitable PAOs include, inter alia, polyethylene oxide $((CH_2CH_2O)_n)$, polypropylene oxide $((CH(CH_3)CH_2O)_n)$ or a polyethylene/polypropylene oxide copolymer $((CH_2CH_2O)_n-(CH(CH_3)CH_2O)_n)$. Other straight, branched chain and optionally substituted synthetic polymers that would be suitable in the practice of the present invention are well known in the medical field.

Most commonly, the chemical group attached to the hemoglobin is polyethylene glycol (PEG), because of its pharmaceutical acceptability and commercial availability. PEGs are polymers of the general chemical formula $H(OCH_2CH_2)_n OH$, where n is generally greater than or equal to 4. PEG formulations are usually followed by a number that corresponds to their average molecular weight. For example, PEG-200 has an average molecular weight of 200 and may have a molecular weight range of 190-210. PEGs are commercially available in a number of different forms, and in many instances come preactivated and ready to conjugate to proteins.

An important aspect of exemplary embodiments of the present invention is that surface modification takes place when the hemoglobin is in the oxygenated or "R" state. This is easily accomplished by allowing the hemoglobin to equilibrate with the atmosphere (or, alternatively, active oxygenation can be carried out) prior to conjugation. By performing the conjugation to oxygenated hemoglobin, the oxygen affinity of the resultant hemoglobin is enhanced. Such a step is generally regarded as being contraindicated, since many researchers describe deoxygenation prior to conjugation to diminish oxygen affinity. See, e.g., U.S. Pat. No. 5,234,903.

Although in many respects the performance of PAO modified hemoglobins is independent of the linkage between the hemoglobin and the modifier (e.g. PEG), it is believed that the type of linkers such as more rigid unsaturated aliphatic or aromatic $C_1$ to $C_6$ linker substituents may change the manufacturing and/or characteristics of the conjugates when compared to those that have different linkages, such as more deformable modes of attachment when compared to the rigid linkers just described.

The number of PEGs to be added to the hemoglobin molecule may vary, depending on the size of the PEG. However, the molecular size of the resultant modified hemoglobin should be sufficiently large to avoid being cleared by the kidneys to achieve the desired half-life. Blumenstein, et al., determined that this size is achieved above a molecular weight of 84,000 Daltons. (Blumenstein, et al., in "Blood Substitutes and Plasma Expanders," Alan R. Liss, editors, New York, N.Y., pages 205-212 (1978).) Therein, the authors conjugated hemoglobin to dextran of varying molecular weight. They reported that a conjugate of hemoglobin (with a molecular weight of 64,000 Daltons) and dextran (having a molecular weight of 20,000 Daltons) "was cleared slowly from the circulation and negligibly through the kidneys," but increasing the molecular weight above 84,000 Daltons did not alter the clearance curves. Accordingly, as determined by Blumenstein, et al., it is preferable that the HBOC have a molecular weight of at least 84,000 Daltons.

In one embodiment of the present invention, the HBOC is a "MalPEG-Hb," which stands for hemoglobin to which malemidyl-activated PEG has been conjugated. Such MalPEG-Hb may be further referred to by the following formula:

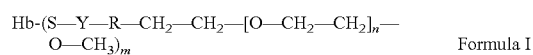

$$Hb\text{-}(S\text{—}Y\text{—}R\text{—}CH_2\text{—}CH_2\text{—}[O\text{—}CH_2\text{—}CH_2]_n\text{—}O\text{—}CH_3)_m \qquad \text{Formula I}$$

where Hb refers to tetrameric hemoglobin, S is a surface thiol group, Y is the succinimido covalent link between Hb and Mal-PEG, R is absent or is an alkyl, amide, carbamate or phenyl group (depending on the source of raw material and the method of chemical synthesis), $[O\text{—}CH_2\text{—}CH_2]_n$ are the oxyethylene units making up the backbone of the PEG polymer, where n defines the length of the polymer (e.g., MW=5000), and $O\text{—}CH_3$ is the terminal methoxy group.

Formulation

The HBOCs of the present invention are formulated by mixing the HBOC and other optional excipients with a suitable aqueous solution, or "diluent" (i.e., one which is pharmaceutically acceptable for intravenous injection.) Although the concentration of the oxygen carrier in the diluent may vary according to the application, and in particular based on the expected post-administration dilution, in preferred embodiments, because of the other features of the compositions of the present invention that provide for enhanced oxygen delivery and therapeutic effects, it is usually unnecessary for the concentration of hemoglobin in an HBOC to be above 6 g/dl, and may be between 0.1 to 4 g/dl.

Suitable diluents may also include, inter alia, proteins, glycoproteins, polysaccharides, and other colloids. It is not intended that these embodiments be limited to any particular diluent. Thus, it is intended that the diluent encompass aqueous cell-free solutions of albumin, other colloids, or other non-oxygen carrying components. In some embodiments, the aqueous solution may have a viscosity of at least 2.5 cP. In other embodiments, the viscosity of the aqueous solution is between 2.5 and 4 cP.

Administration of the compositions described herein may occur at any time "in connection with surgery", including as long as a day before, during or a day after surgery.

Clinical Applications

The present invention relates to HBOCs such as PAO modified hemoglobin conjugates that may exhibit less cooperativity than native hemoglobin that are formulated into compositions with lower P50s than whole blood, which in some embodiments are less than half the P50 of whole blood. Such compositions are useful to enhance hemodynamic stability in normovolemic patients undergoing surgery. They may be administered using the same administration parameters that are well known in the art for plasma expanders, volume enhancers and such. Hemodynamic stability may be monitored before, during or after surgery, or any combination thereof. Thus, enhancement of hemodynamic stability is not necessarily limited to the measurement of the hemodynamic properties of the subject just during the surgical procedure itself, and may be observed any time post-administration.

The patient population that may benefit the most from the practice of the present invention method is "normovolemic patients undergoing surgery." Thus, in one embodiment, the present invention method relates to the administration of the compositions to patients that have not undergone the extraction of blood during an acute normovolemic hemodilution (ANH) treatment. This is based on the finding that individuals receiving these compositions in connection with a surgical procedure are less likely to require a blood transfusion during or after surgery. Hence, the methods of the present invention are, in one aspect, an alternative to ANH.

In another aspect, the present invention method may also result in the indirect benefit of a normovolemic patient undergoing surgery requiring less administration of vasopressors during surgery to raise blood pressure, because their blood pressure is effectively stabilized during surgery due to the prophylactic administration of the HBOC in connection with the surgery.

EXAMPLES

A similar version of the following three Examples are disclosed U.S. Patent Application No. 2003/0162693, which published on Aug. 28, 2003. As for all of the Examples, MalPEG-Hb is used as a model HBOC. The production and availability of other HBOCs are well known in the scientific literature, yet the ability to conduct clinical trials in human subjects is carefully regulated and impossible to perform using multiple forms of HBOCs. Thus, based on the teachings presented herein it should be well understood to one of skill in the art that the scope of the present invention is not limited to the use of MalPEG-Hb, and HBOCs with similar characteristics (e.g., a higher oxygen affinity than native hemoglobin, and in particular PAO modified hemoglobin) would also be suitable for use.

Example 1

Production of Stroma-Free Hemoglobin

Step 1: Procurement of Outdated Red Blood Cells

Outdated packed red blood cells are procured from a commercial source, such as the San Diego Blood Bank or the American Red Cross. Preferably, outdated material is received not more than 45 days from the time of collection. Packed RBCs (pRBCs) are stored at 4±2° C. until further processed (1-7 days). All units are screened for viral infection and subjected to nucleic acid testing prior to use.

Step 2: Pooling of Outdated Blood

Packed red blood cells are pooled into a sterile vessel in a clean facility. Packed red blood cell volume is noted, and hemoglobin concentration is determined using a commercially available co-oximeter or other art-recognized method.

Step 3: Leukodepletion

Leukodepletion (i.e. removal of white blood cells) is carried out using membrane filtration. Initial and final leukocyte counts are made to monitor the efficiency of this process.

Step 4: Cell Separation and Cell Wash

Red blood cells are washed with six volumes of 0.9% sodium chloride. The process is carried out at 4±2° C. The cell wash is analyzed to verify removal of plasma components by a spectrophotometric assay for albumin.

Step 5: Red Blood Cell Lysis and Removal of Cell Debris

Washed red blood cells are lysed at least 4 hours or overnight at 4±2° C. with stirring using 6 volumes of water. Lysate is processed in the cold to purify hemoglobin. This is achieved by processing the lysate through a 0.16-μm membrane. Purified hemoglobin is collected in a sterile depyrogenated vessel. All steps in this process are carried out at 4±2° C.

Step 6: Viral Removal

Viral removal is performed by ultrafiltration at 4±2° C.

Step 7: Concentration and Solvent Exchange

Hemoglobin purified from lysate and ultrafiltration is exchanged into Ringer's lactate (RL) or phosphate-buffered saline (PBS, pH 7.4) using a 10 ID membrane. The hemoglobin is then concentrated using the same membrane to a final concentration of 1.1-1.5 mM (in tetramer). Ten to 12 volumes of RL or PBS are used for solvent exchange. This process is carried out at 4±2° C. The pH of the solution prepared in RL is adjusted to 7.0-7.6.

Step 8: Sterile Filtration

Hemoglobin in PBS or Ringer's lactate (RL) is sterile-filtered through a 0.45- or 0.2-μm disposable filter capsule and stored at 4±2° C. before the chemical modification reaction is performed.

Other methods for purifying hemoglobin are well known in the art. In addition, the use of a reducing agent (e.g. glutathione or another thiol-containing reducing agent) to prevent auto-oxidation after cell lysis is usually unnecessary.

Example 2

Modification of Stroma Free Hemoglobin

Step 1: Thiolation

Thiolation is carried out using 10-fold molar excess iminothiolane over hemoglobin for 4 hours at 4±2° C. with continuous stirring.

Reaction conditions:

1 mM hemoglobin (tetramer) in RL (pH 7.0-7.5) or PBS (pH 7.4)

10 mM iminothiolane in RL (pH 7.0-7.5) or PBS (pH 7.4)

The ratio of 1:10 SFH:iminothiolane and reaction tuning were optimized to maximize the number of PEGylated thiol groups and to minimize product heterogeneity.

Step 2: PEGylation of Thiolated Hemoglobin

Thiolated hemoglobin is PEGylated using a 20-fold molar excess of Mal PEG (with an alkyl or phenyl linker) based on starting tetrameric hemoglobin concentration. The hemoglobin is first allowed to equilibrate with the atmosphere to oxygenate the hemoglobin. The reaction takes place for 2 hours at 4±2° C. with continuous stirring.

Reaction conditions:

1 m thiolated hemoglobin in RL or PBS (pH 7.4)

20 mM Mal-PEG in RL or PBS (pH 7.4)

Step 3: Removal of Unreacted Reagents

PEGylated-Hb is processed through a 70-kD membrane to remove excess unreacted reagents or hemoglobin. A 20-volume filtration is carried out to ensure removal of unreacted reagents, which is monitored by size-exclusion chromatography at 540 nm and 280 nm, The protein concentration is diluted to 4 g/dl. The pH is adjusted to 7.3±0.3 using 1 N NaOH.

Step 4: Sterile Filtration

The final MalPEG-Hb product is sterile-filtered using a 0.2-μm sterile disposable capsule and collected into a sterile depyrogenated vessel at 4±2° C.

Step 5: Formulation of MalPEG-Hb

PEGylated Hb is diluted to 4 g/dl RI, pH adjusted to 7.4±0.2.

Step 6: Sterile Fill

The final blood substitute composition is sterile-filtered (0.2 μm) and aliquoted by weight into sterile glass vials and closed with sterile rubber stoppers with crimped seals in a laminar flow hood and stored at −80° C. until use.

Example 3

Physiochemical Analysis of MalPEG-Hb

Methodology for Physicochemical Analysis

Homogeneity and molecular size of the MalPEG-Hb blood substitute are characterized by Liquid Chromatography (LC). Analytical LC is used to evaluate homogeneity of the PEGylated hemoglobin and extent of removal of unreacted MalPEG. Absorbance at 540 urn is used to evaluate hemoglobin and resolves PEGylated hemoglobin from unreacted hemoglobin by peak position. Absorbance at 280 nm is used to resolve PEGylated hemoglobin from free Mal-PEG, which absorbs in the ultraviolet (UV) spectrum due to the ring structures in MalPEG.

Optical spectra are collected using a rapid scanning diode array spectrophotometer (Milton Roy 2000 or Hewlett Packard Model 8453) in the Soret and visible regions for analysis of hemoglobin concentration and percent methemoglobin by multicomponent analysis (Vandegriff K. D., and R. E., Shrager. Evaluation of oxygen equilibrium binding to hemoglobin by rapid-scanning spectrophotometry and singular value decomposition. Meth. Enzymol. 232: 460-485 (1994).

MalPEG-Hb concentration and percentage methemoglobin are determined using a co-oximeter. Viscosity is determined using a Rheometer. Colloid Osmotic Pressure is determined using a colloid osmometer. Oxygen binding parameters are determined from oxygen equilibrium curves.

Exemplary specifications for the blood substitute composition are presented in Table 1 below:

TABLE 1

| Test | Specification |
|---|---|
| Hemoglobin concentration (g/dl) | 4.2 ± 0.2 |
| Methemoglobin (%) | <10 |
| pH | 7.4 ± 0.4 |
| Conductivity (mS/cm) | 12 ± 4 |
| Endotoxin (EU/mL) | <0.5 |
| FPLC retention time (min) | 43 ± 3 |
| FPLC peak width at half height (min) | 6 ± 2 |
| Viscosity (cPs) | 2.5 ± 1.0 |
| COP (mmHg) | 50 ± 20 |

TABLE 1-continued

| Test | Specification |
|---|---|
| P50(Torr) | 6 ± 2 |
| Hill number (at P50) | 1.2 ± 0.5 |
| Sterility | Pass |

Number of PEGylated Sites on MalPEG-Hb

For surface modification, the number "m" in Formula I is the parameter that defines the number of PEG polymers attached to the surface of hemoglobin.

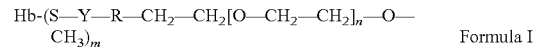

$$\text{Hb-(S—Y—R—CH}_2\text{—CH}_2\text{[O—CH}_2\text{—CH}_2\text{]}_n\text{—O—CH}_3\text{)}_m \quad \text{Formula I}$$

To determine this number, a dithiopyridine colorimetric assay (Ampulski R., V. Ayers, and S. Morell. Determination of the reactive sulfhydryl groups in heme proteins with 4,4'-dipyridinesdisulde. *Biocheim. Biophys. Acta* 163-169, 1969) is used to measure the number of available thiol groups on the surface of the Hb tetramer before and after violation and then again after Hb PEGylation. Human hemoglobin contains 2 intrinsic reactive thiol groups at the 093Cys residues, which is confirmed by the dithiopyridine reaction. After thiolation of SFH at a ratio of 1:10 SFH:iminothiolane, the number of reactive thiol groups increases from 2 to 6 thiols based on the dithiopyridine reaction. After the PEGylation reaction, the number of reactive thiol groups is decreased to 1.3. This indicates that there are 4-5 PEGylated sites on MaLPEG-Hb.

Size-Exclusion Chromatography Analysis of MalPEG-Hb Versus SFH

FPLC is performed for analysis of the final MaLPEG-Hb product. Typical chromatograms are displayed in FIG. 1 for MaLPEG-Hb compared to unmodified SFH. The retention time for SFH is approximately 57 mm. The retention time for MaLPEG-Hb is approximately 44 Min.

Physical and Chemical Characteristics of MalPEG-Hb

The physical properties of MalPEG-Hb compared to blood and unmodified human hemoglobin (SFH) are shown below in Table 2.

TABLE 2

| | Blood | SFH | MalPEG-Hb |
|---|---|---|---|
| P50(Torr) | 28 | 15 | 5 |
| N50 (Hill number) | 2.9 | 2.9 | 1.2 |
| Bohr effect (ΔLog P50/ΔpH) | — | −0.46 | −0.20 |
| Viscosity (cPs) | 4.0 | 0.9 | 2.5 |
| COP (mm Hg)[1] | 27 | 16 | 50 |
| MW (kD)[2] | N/A | 65 | 90 |
| Molecular Radius (nm) | 4000 | 3.2[2] | 9 |

Figure 2:
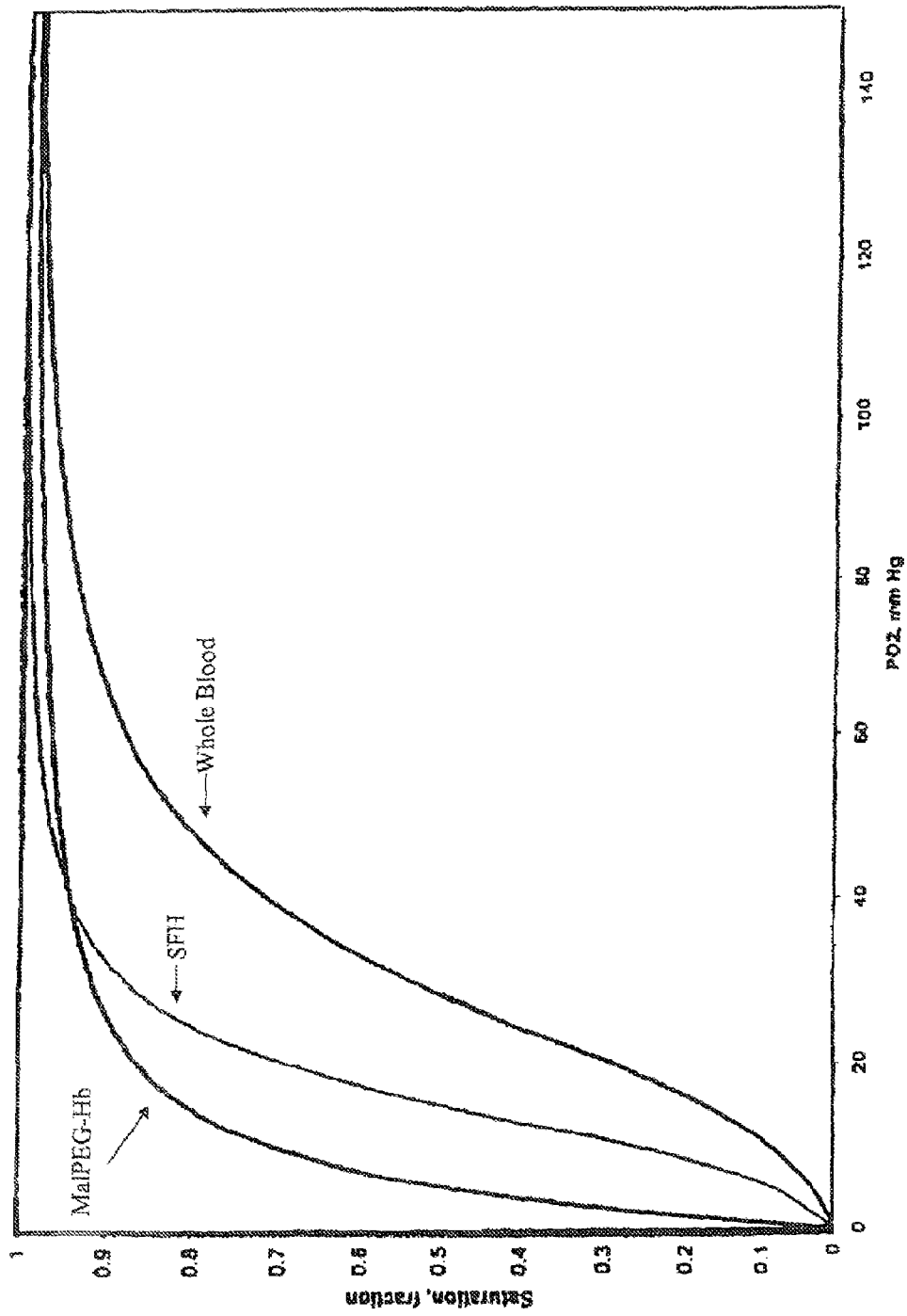
FIG. 2 depicts oxygen equilibrium curves for MalPEG-Hb, SFH and whole blood.
Figure 3:
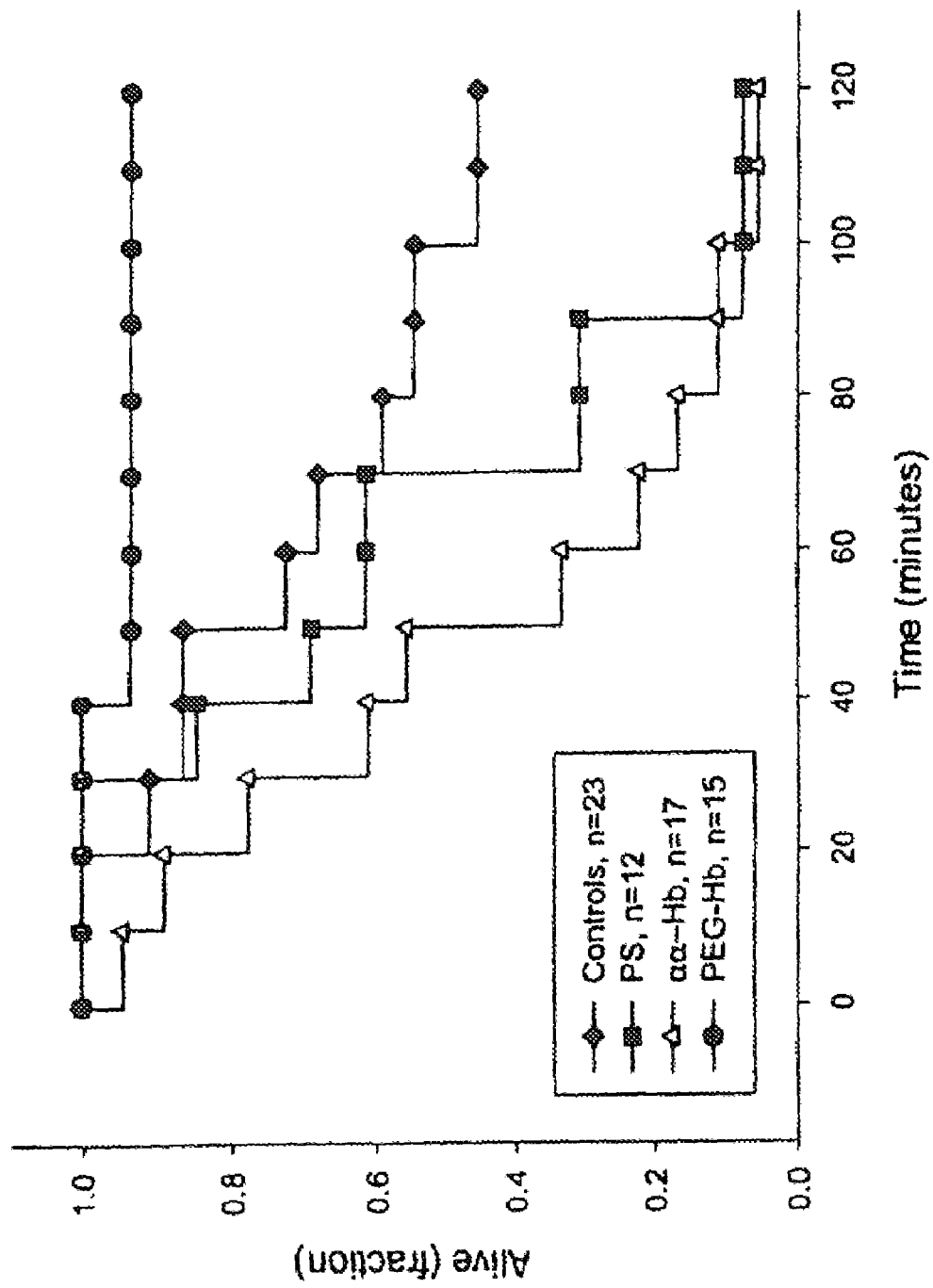
FIG. 3 depicts the survival rate of rats after administration of various test solutions.

[1]Determined at 15 g/dl for whole blood and approximately 4 g/dl for hemoglobin solutions
[2]Determined by COP measurements and FPLC Oxygen Affinity Hemoglobin-oxygen equilibrium binding curves were measured during enzymatic oxygen consumption. (*Anal Biochem.* 256: 107-116, 1998). MalPEG-Hb exhibits a high oxygen affinity (P50= 5 mm Hg) and low cooperativity (n50= 1.0-1.4). FIG. 2 shows representative curves comparing stroma-free hemoglobin (SFH), MalPEG-Hb and blood.

Viscosity

This solution property of MalPEG-Hb is due to the strong interaction between polyethylene glycol chains and solvent water molecules. This is believed to be an important attribute for a MalPEG-Hb blood substitute for two reasons: 1) higher viscosity decreases the diffusion constant of both the PEG-Hb molecule and gaseous ligand molecules diffusing through the solvent, and 2) higher viscosity increases the shear stress of the solution flowing against the endothelial wall, eliciting the release of vasodilators to counteract vasoconstriction. As shown in Table 2, the viscosity of the MalPEG-Hb solution is 2.5 cPs.

Colloidal Osmotic Pressure (COP)

The COP of hemoglobin solutions containing unmodified, intra- and intermolecularly cross-linked, or PEG-surface-conjugated hemoglobin have been measured to determine their macromolecular solution properties (Vandegriff, K. D., R. J. Rohlfs, and R. M. Wislow. *Colloid osmotic effects of hemoglobin-based oxygen carriers*. In Winslow, R. M., K. D. Vandegriff and M. Intaglia, eds, Advances in Blood Substitutes Industrial Opportunities and Medical Challenges. Boston, Birkhauser, pp. 207-232 (1997). Tetrameric hemoglobins show nearly ideal solution behavior; whereas hemoglobins conjugated to PEG have significantly higher colloid osmotic activity and exhibit solution non-ideality (Vandegriff, K. D., M. Mcarthy, R. J. Rohls and R. M. Winslow. Colloid osmotic properties of modified hemoglobins: chemically cross-linked versus polyethylene glycol surface conjugated. Biophys. Chem. 69:23-30 (1997). As shown in Table 2, the COP of the MalPEG-Hb solution is 50.

Stability

The stability of hemoglobin solutions containing PEG-hemoglobin have been determined by examining the rate of autoxidation. At room temperature, the autoxidation of MalPEG-Hb increased from approximately 5% MetHb to 5.5% MetHb in 10 hours. The autoxidation rate for MalPEG-Hb was therefore 0.05% per hour.

Example 4

Stability of MalPEG-Hb

The purpose of this study was to determine the stability of MalPEG-Hb during a simulation of exemplary storage and handling conditions. The stability during three stages of handling was assessed. Stage I represented the transfer from frozen storage at the production facility to temperature conditions during shipping to the clinical site (frozen storage study). Stage II represented the thawing of the MalPEG-Hb for 24 hours to +4° C. and subsequent storage at +4° C. for five days (refrigerated study). Stage III represented the thawing of the MalPEG-Hb for 24 hours to +4° C. and subsequent storage of MalPEG-Hb at room temperature for several days prior to patient administration (room temperature study).

Experimental Methods

Stability was defined by the rate of oxidation of the MalPEG-Hb test material. The percentage of methemoglobin in the sample was measured using co-oximetry (IL Co-Oximeter 682, GMI, Inc., Ramsey, Minn.) Measurements were made in duplicate at each time point according to the protocol.

Temperatures were monitored by thermometer or temperature chart recorders. The frozen storage study was conducted over a temperature range of −21.0±3.0° C. The refrigerated study was conducted over a temperature range of +4.0±0.2° C. The room temperature study was conducted over a temperature range of +21.0±1.0° C.

Temperature, total hemoglobin, and percent methemoglobin were recorded at each of the indicated time points. In the frozen and refrigerated studies, measurements were taken at time zero (completely thawed), one hour later, and then every 24 hours for five days. In the room temperature study, measurements were taken at time zero (completely thawed) and subsequently every one hour for ten hours.

Results

MalPEG-Hb exhibited no significant change in percent methemoglobin during 6 day storage at −20° C. Similarly, MalPEG-Hb showed no appreciable change in percent methemoglobin during five day storage at +4° C. During storage at room temperature, MalPEG-Hb showed less than 1 percent increase in methemoglobin over a ten hour period.

Example 5

Use of Mal-PEG to Promote Hemodynamic Stability

Figure 4:
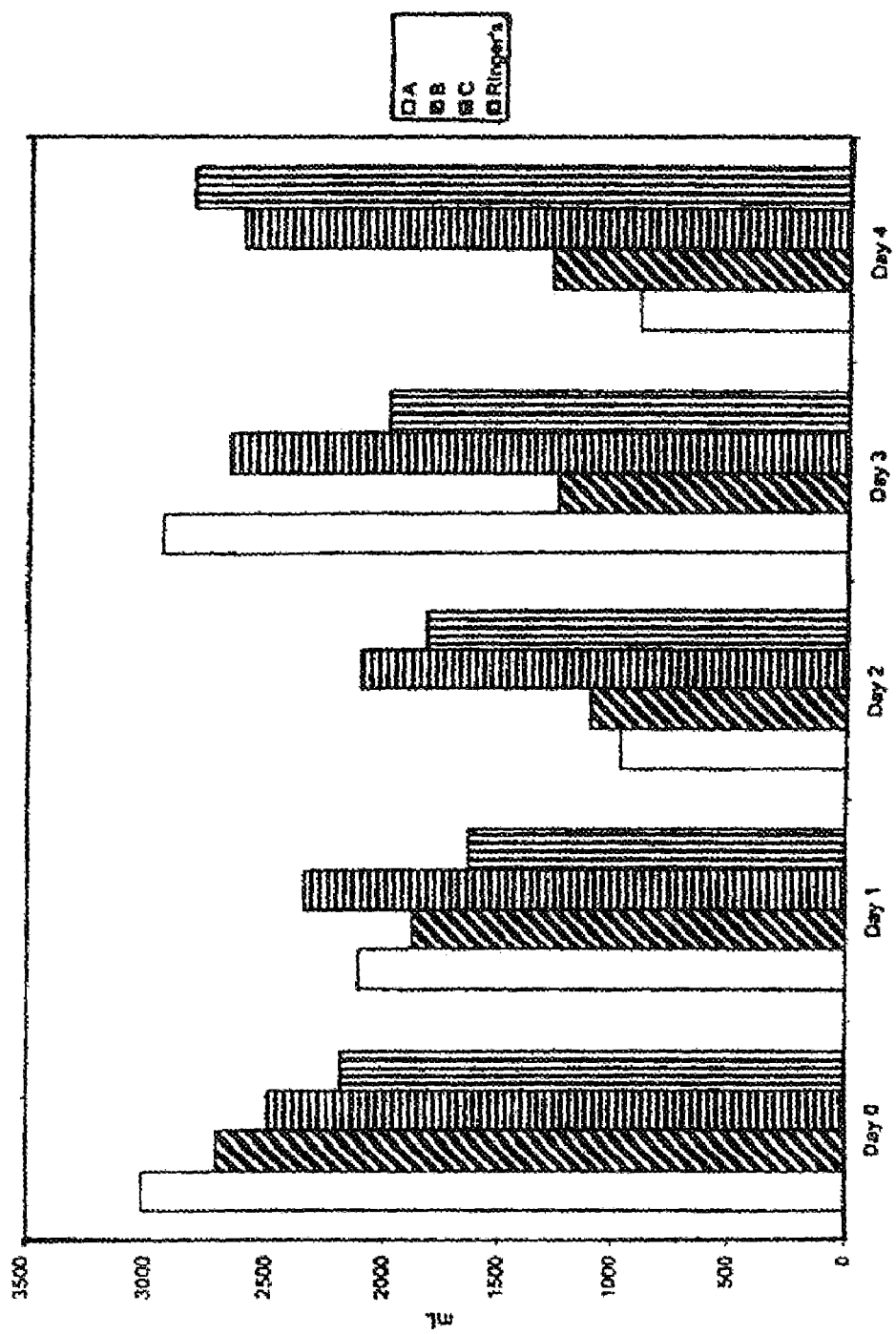
FIG. 4 depicts the urine output of patients receiving MalPEG-Hb or Ringer's Lactate.

MalPEG-Hb was prepared as described above. A dosage of 0 (Lactated Ringer's alone), 200 ("A"), 400 ("B") or 600 mL ("C") of MalPEG-Hb, balanced to a total volume of 1000 mL Lactated Ringer's, was administered to patients undergoing elective orthopedic surgery prior to spinal anesthesia induction. The results are depicted in FIG. 4.

Figure 5:
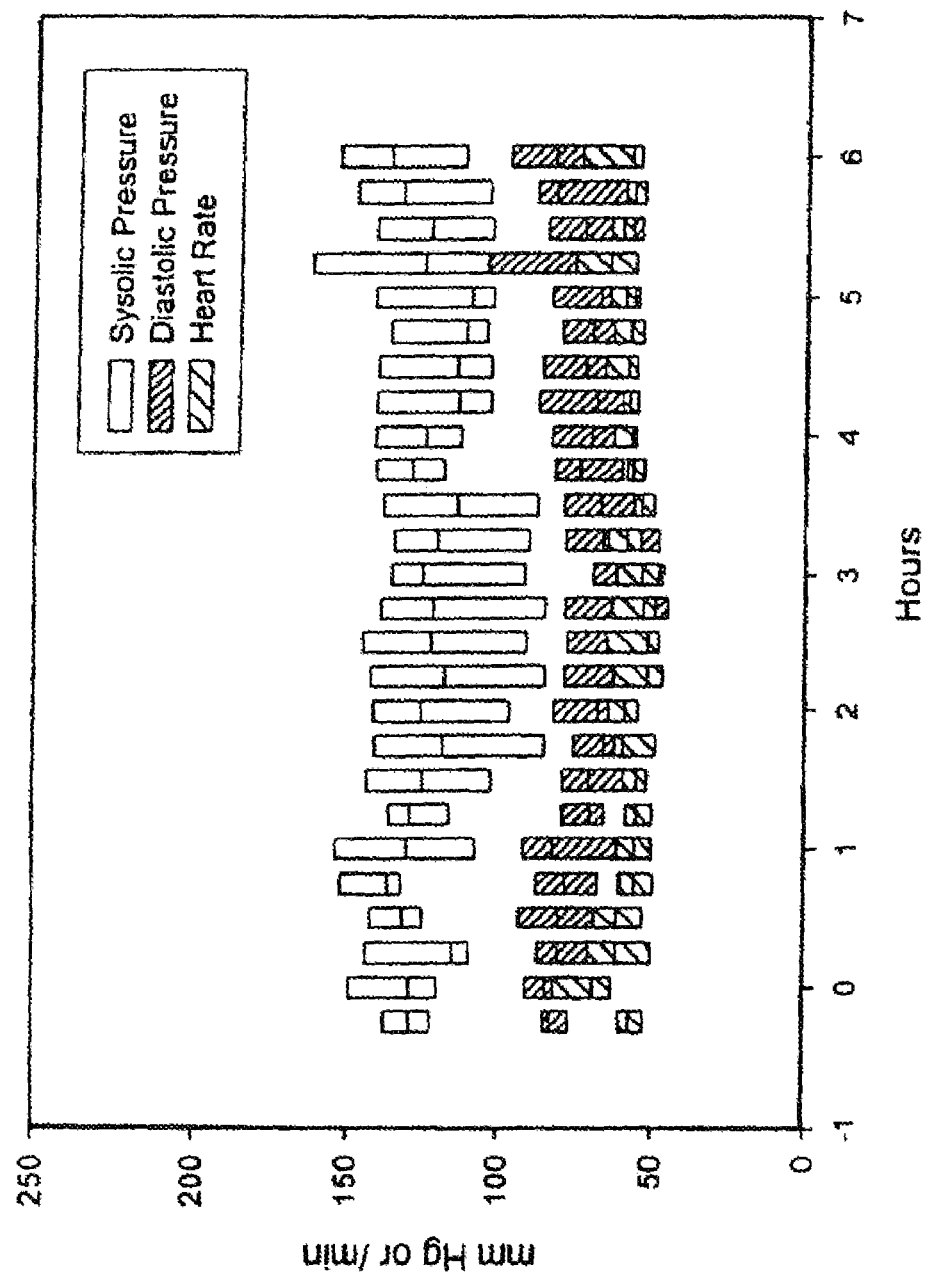
FIG. 5 depicts vital signs of patients receiving MalPEG-Hb prior to anesthesia.

FIG. 5 depicts the vital signs of patients that received 600 mL MalPEG Hb. As shown, no elevations of blood pressure were observed compared to baseline measurements. In contrast, detectable but slight blood pressure increases were observed in patients that received 200 or 400 mL MalPEG-Hb.

Hypotensive events were also monitored in patients, and the results are shown below in Table 3:

TABLE 3

|  | 200 mL | 400 mL | 600 mL | Ringer's Lactate |
|---|---|---|---|---|
| No. of Patients with Hypotension | 0 | 2 | 0 | 2 |
| No. of Episodes per Patient | 0 | 2 | 0 | 3 |
| No. of Interventions | 0 | 0 | 0 | 2 |

As shown, the patients receiving MalPEG-Hb demonstrated less hypotensive events than the patients receiving the placebo.

Example 6

Expanded Clinical Study of the Use of MalPEG-Hb to Enhance Hemodynamic Stability During Surgery MalPEG-Hb has previously been tested in a Phase I trial in healthy volunteers and yielded no significant adverse events, and was also consistent with nonclinical studies showing reduced vasoactivity compared to stroma-free Hb. Hemodynamic instability (e.g., cardiovascular events) measured as hypotensive events, particularly in elderly patients with cardiovascular disease, are a concern for such patients undergoing surgery. Considerable literature supports the hypothesis that such hypotension produces ischemia in the brain, heart and kidneys that could lead to significant postoperative morbidity. The development of Hb-based oxygen carriers (HBOCs) to protect such surgical patients from the effects of these adverse events is the focus of this experiment.

A randomized, double-blind study of MalPEG-Hb (250 or 500 mL) and a control group receiving Ringer's acetate alone, was carried out at 6 different hospitals in groups of 30 patients each. Consenting patients underwent major invasive surgery, predominantly hip replacement Dosing occurred prior to induction of spinal anesthesia. Safety assessment included vital signs and Holter monitoring (from infusion to 24 hours), as well as clinical chemistry, coagulation, hematology, and fluid balance. The incidence of hypotension, defined quantitatively as systolic pressure less than 90 mmHg or 75% of the baseline value, was the primary efficacy endpoint. Another measure of efficacy was the necessity for pharmacologic intervention to stabilize blood pressure and fluid balance as more fully described below.

Study Population

The bulk of the patients studied in this experiment were undergoing surgical procedures that were elective, primary hip replacements in patients with osteoarthritis. However, a number of acute fractures were also studied, as well as a few secondary replacements. Inclusion and exclusion criteria are presented in Table 4.

Hb were removed from the freezer (−20° C.) and placed at room temperature for gradual thawing. Ringer's acetate was obtained from a commercial source (Fressenius Kabi A B, Uppsala, Sweden.)

Administration

Either MalPEG-Hb or placebo was administered through an established intravenous line via a calibrated volumetric infusion pump. A total volume of 1000 mL of MalPEG-Hb and/or Ringer's acetate was infused for blinding purposes before anesthesia was induced, which took place within 30 minutes after the end of infusion.

Infusion of the test composition or placebo solution did not influence normal care of the patient. Patients receiving either test or placebo solution also received any additional treatments deemed necessary for the well being of the patient. All medical procedures and treatments were conducted according to the clinic's standard care. The administration of all continuous medication on-going at study start and concomi-

TABLE 4

| Inclusion Criteria | Exclusion Criteria |
|---|---|
| Adult males or females (surgically sterile or postmenopausal) ASA class I-III patients aged ≧50 years, undergoing spinal anesthesia for acute hip fracture surgery (internal fixation or replacement) or elective hip replacement surgery | Any acute or chronic condition which would limit the patient's ability to complete the study or jeopardize the safety of the patient as judged by the investigator |
| Stable for surgery and anesthesia as determined by physical examination, laboratory status, vital signs and ECG as judged by the investigator | Patients with clinical manifestations of uncontrolled metabolic, cardiovascular or psychiatric disorder |
| Has been given written and verbal information and has had opportunity to ask questions about the study | Blood pressure >180 mmHg (systolic) or >105 mmHg (diastolic) measured in a supine position at screening |
| Patients must sign an Informed Consent Form (see Appendix II) for the study, which has been reviewed and approved by the Independent Ethics Committee (IEC) | Patients with recent history of myocardial infarction or stroke (within 6 months) |
| | Patients with recent history of myocardial infarction or stroke (within 6 months) |
| | Patients with recent history of myocardial infarction or stroke (within 6 months) |
| | Known alcohol or other drug dependency |
| | Patients who have received any other investigational drugs within 30 days prior to administration of the study drug |
| | Patient on oral anti-coagulant treatment with the exception of low-dose (<200 mg/day) acetylsalicylic acid |
| | History or family history of a hemoglobinopathy |
| | History of coagulopathy |
| | Professional or ancillary personnel involved with this study |

Randomization and Blinding

The treatment assigned to each numbered patient was determined according to a computer generated, sequentially numbered randomization code list. The treatment groups were designated: A, 250 mL of MalPEG-Hb; B, 500 mL of MalPEG-Hb; (A and B representing the "test groups") and C, Ringer's acetate (representing the "placebo group"), with all administration volumes for each group being adjusted to the same total administration volume prior to administration. As MalPEG-Hb is red in color and the placebo is transparent, efforts were also undertaken to prevent the patient and "blinded" staff from seeing the solution being infused, i.e. the study was performed in classical "double blinded" fashion.

Materials

MalPEG-Hb was prepared essentially as described above in Examples 1 to 3 with some minor variations. Approximately 24 hours before administration, bottles of MalPEGtant medication given during the study were noted and considered in interpreting the results.

Pharmacokinetic Measurements and Variables

The intravascular persistence of MalPEG-Hb and intravascular product stability were determined from plasma hemoglobin and methemoglobin levels prior to infusion, end of infusion, 6 hours after infusion, days 1, 2 and 3 and 7-10 days post infusion. The results of these studies were not out of the ordinary and are not reported herein.

Sample Collection and Analysis

Blood samples were drawn using routine methods to minimize hemolysis during sampling and processed to insure complete separation of blood samples from plasma. As the plasma portion of blood samples containing MalPEG-Hb were red, it was necessary for sample processing to be performed by an "unblended" technician. Sample analysis was performed before "code breaking." Thus, the laboratory performing the analysis was appropriately blinded.

Efficacy Measurements and Variables

The effectiveness of MalPEG-Hb as an exemplary HBOC for enhancing hemodynamic stability was studied using the following endpoints:

A. Hypotensive Episodes

The number of hypotensive episodes after infusion of MalPEG-Hb/Placebo, was defined as a systolic blood pressure (SBP) <90 mmHg or a ≧25% drop in SBP compared to pre-infusion. Each registration of a SBP fulfilling the definition was counted as one hypotensive episode.

B. Total Fluid Intake and Output (Fluid Balance)

Measurement were made on the day of surgery (from start of infusion to 24 hours after start of infusion) and post-operative days 1, 2 and 3. Intake included: infused fluids (MalPEG-Hb/Placebo, colloids and crystalloids), blood transfusions and oral fluid intake. Output included: urine and the estimated blood loss during surgery.

The type and amount of intravenous fluids were recorded (data not shown.) The total amount of crystalloid and colloid infusions were not statistically different among the three groups for the entire hospitalization period. However, differences did occur in the intraoperative period. Group A received significantly less crystalloid (913±106 mL) compared to Group B (1299±183 mL) and Group C (1281±144 mL) (P<0.05). Furthermore, when the MalPEG-Hb was included in the amount of colloid administered, Group B received significantly more total colloid (1389±169 mL) compared to Group A (850±66 mL) or Group C (666±69 mL). Both differences, B vs C and A vs B were statistically significant (P<0.05). There were no statistically significant differences in crystalloid, colloid or total intravenous fluid administration for the remainder of the study.

C. Cardiac Disturbances

The number and type of cardiac disturbances as measures of hemodynamic instability (tachycardia, ischemia, bradycardia and conduction problems) were evaluated by the blinded cardiologist. Cardiac rhythm disturbances were recorded using continuous Holter-monitoring and ECG.

D. Pharmacological Interventions

The number and dose of pharmacological interventions (e.g. blood pressure drugs, diuretics) for cardiovascular support were also recorded from anesthesia induction through 12 hours after start of infusion.

E. Blood Transfusions

Blood transfusions (volume of packed red blood cells) administered during surgery (from anesthesia induction to end of surgery and afterward) were also recorded F. Oxygen Utilization Duration of post-operative supplemental oxygen administration was recorded on the day of surgery and for a few days thereafter.

Results

Figure 6:
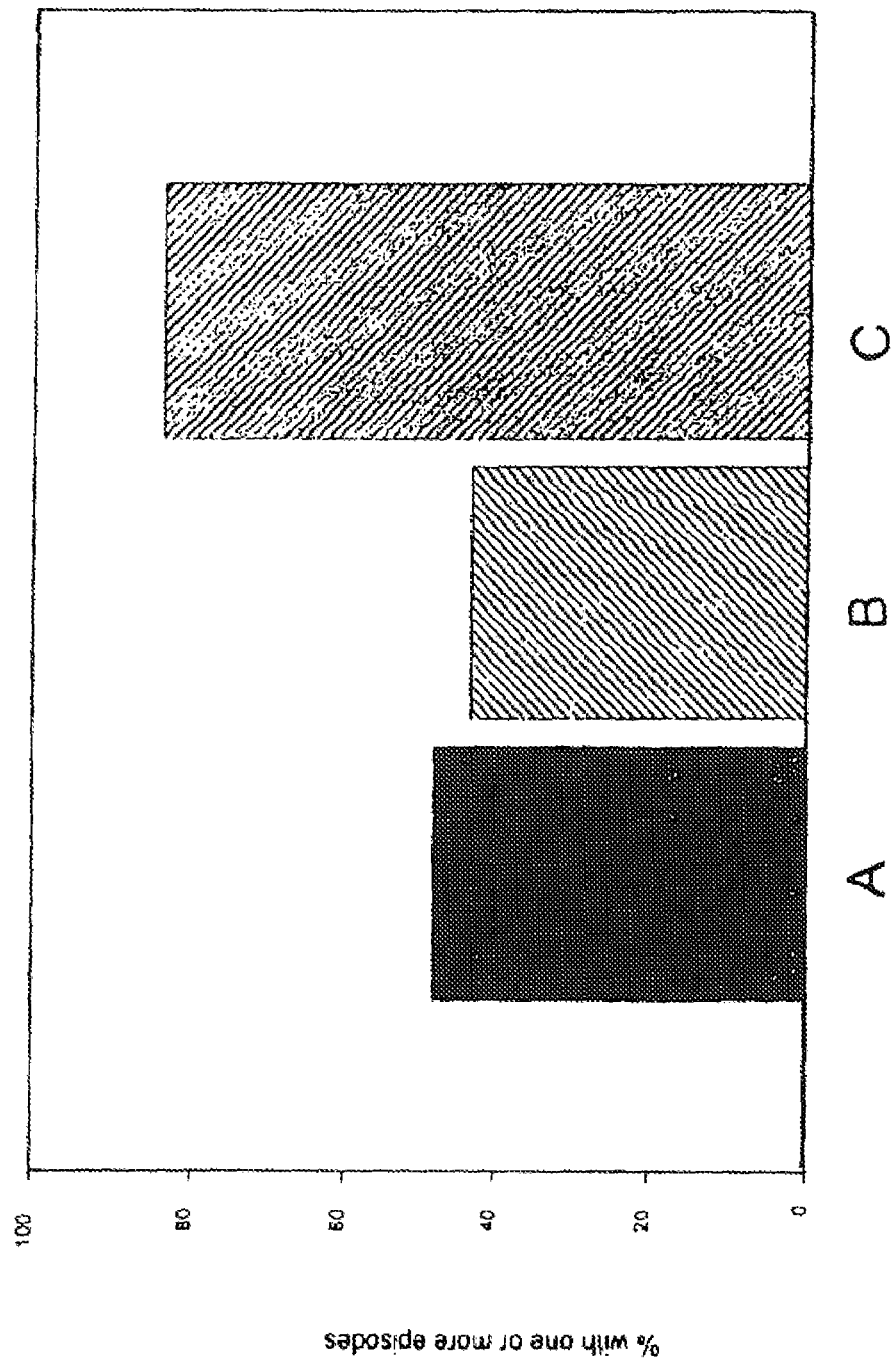
FIG. 6 depicts the percentage of patients receiving MalPEG-Hb or a placebo that exhibit hypotensive events during surgery.

Hypotensive instability manifested as adverse events, such as hypotensive episodes and the necessity for administration of pressors, are shown in Table 5 below. The results obtained for the percent of hypotensive events are also depicted in FIG. 6.

TABLE 5

| Events | Group A (n = 29) | Group B (n = 30) | Group C (n = 31) |
|---|---|---|---|
| Hypotensive events | 15 | 15 | 27 |
| % of Patents with Hypotensive events | 52 | 50 | 87 |
| Number of Patients treated with Pressors | 5 | 4 | 10 |
| % of Patients treated with Pressors | 17 | 13 | 32 |

The examples set forth above are provided to give those of ordinary skill in the art with a complete disclosure and description of how to make and use the preferred embodiments of the compositions, and are not intended to limit the scope of what the inventors regard as their invention. Modifications of the above-described modes (for carrying out the invention mat are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The invention claimed is:

1. A method for reducing hypotensive events that may be experienced by a normovolemic subject during surgery while under general anesthesia, said method comprising the steps of:
   a) providing a modified hemoglobin having an oxygen affinity higher than native hemoglobin in whole blood and a reduced cooperativity relative to native hemoglobin;
   b) administering the modified hemoglobin to the subject before the surgery; and
   c) monitoring blood pressure of the subject after administering the modified hemoglobin and during surgery to detect hypotension;
   wherein the subject did not undergo an acute normovolemic hemodilution treatment in connection with the surgery.

2. The method according to claim 1, wherein the modified hemoglobin further comprises a polyalkylene oxide modified natural hemoglobin.

3. The method according to claim 1, wherein the modified hemoglobin further comprises a polyalkylene oxide modified synthetic hemoglobin.

4. The method according to claim 1, wherein the modified hemoglobin further comprises a polyalkylene oxide modified recombinant hemoglobin.

5. The method according to claim 1, wherein the modified hemoglobin further comprises a polyalkylene oxide modified human hemoglobin.

6. The method according to claim 1, wherein the modified hemoglobin further comprises a polyalkylene oxide modified hemoglobin from a non-human animal.

7. The method according to claim 1, wherein the modified hemoglobin has an oxygen affinity greater than twice that of whole blood.

8. The method according to claim 1, wherein the modified hemoglobin has a P50 between 4 and 15.

9. The method according to claim 1, wherein the modified hemoglobin further comprises hemoglobin that has been modified by covalent attachment of malemidyl-activated polyethylene glycol.

* * * * *